United States Patent
Spahn

(10) Patent No.: US 7,550,728 B2
(45) Date of Patent: Jun. 23, 2009

(54) DIAGNOSIS DEVICE AND DIAGNOSIS METHOD FOR RADIOGRAPHIC AND NUCLEAR MEDICAL EXAMINATIONS

(75) Inventor: Martin Spahn, Chicago, IL (US)

(73) Assignee: Siemens Aktiengesellschaft, Munich (DE)

( * ) Notice: Subject to any disclaimer, the term of this patent is extended or adjusted under 35 U.S.C. 154(b) by 7 days.

(21) Appl. No.: 11/592,307

(22) Filed: Nov. 2, 2006

(65) Prior Publication Data

US 2007/0102642 A1 May 10, 2007

(30) Foreign Application Priority Data

Nov. 10, 2005 (DE) .................. 10 2005 053 993

(51) Int. Cl.
*G01T 1/161* (2006.01)
(52) U.S. Cl. .................. 250/363.02; 250/363.03; 250/363.04; 250/366; 378/4
(58) Field of Classification Search ........... 250/363.03, 250/363.04, 370.09, 366, 367, 363.02; 378/4
See application file for complete search history.

(56) References Cited

U.S. PATENT DOCUMENTS 6,399,951 B1 * 6/2002 Paulus et al. ........... 250/370.13
6,490,476 B1 * 12/2002 Townsend et al. ........... 600/427
6,720,966 B2 * 4/2004 Barth et al. .................. 345/424
2002/0191734 A1 * 12/2002 Kojima et al. .................. 378/4
2005/0258369 A1 * 11/2005 Wieczorek .................. 250/366

FOREIGN PATENT DOCUMENTS

WO   WO 2004/095069 A1   11/2004

OTHER PUBLICATIONS

M. Spahn, V. Heer, R. Freytag, "Flachbilddetektoren in der Röntgendiagnostik", Der Radiologe, 2003, pp. 340-350, ISSN 0033-832X, vol. 43, Springer, Berlin, Allemagne.
Heinz Morneburg, "Nuklearmedizin", Bildgebende Systeme für die medizinische Diagnostik, 1995, pp. 470-499, Chapter 10, MCD Verlag.

\* cited by examiner

*Primary Examiner*—David P Porta
*Assistant Examiner*—Casey Bryant

(57) ABSTRACT

The invention relates to a diagnosis device for combined or combinable radiographic and nuclear medical examinations with: an x-ray source, an examination room for accommodating a patient, a gamma radiation source arranged in the body of a patient, a detector system for simultaneously measuring the x-ray and gamma radiation without changing the patient's position. The diagnosis device implements the radiographic examination by evaluating the measurement of the x-rays and implements a single photon emission SPE examination as a nuclear examination by evaluating the gamma radiation.

18 Claims, 3 Drawing Sheets

DIAGNOSIS DEVICE AND DIAGNOSIS METHOD FOR RADIOGRAPHIC AND NUCLEAR MEDICAL EXAMINATIONS

CROSS REFERENCE TO RELATED APPLICATIONS

This application claims priority of German application No. 10 2005 053 993.9 filed Nov. 10, 2005, which is incorporated by reference herein in its entirety.

FIELD OF THE INVENTION

The invention relates to a diagnosis device for combined or combinable radiographic and nuclear medical examinations having an x-ray source, an examination room for accommodating a patient with a gamma radiation source arranged in the body, a detector system for simultaneously measuring the x-ray and the gamma radiation without changing the patient's position, with the diagnosis device being designed in order to carry out the radiographic examination as well as a corresponding diagnosis method by evaluating the measurement of the x-rays.

BACKGROUND OF THE INVENTION

Digital imaging methods have now become common practice in medical diagnostics. Methods of this type have been used for years, e.g. in computer tomography, for magnetic resonance examinations, ultrasound examinations and for nuclear medical methods.

The publication WO 2004/095069 A1 discloses a detector element for the combined detection of x-rays and gamma radiation. This detector element has a converter, which generates a charge signal as a function of incident x-ray or gamma quanta. In an evaluation device which is arranged downstream, the charge signal is amplified and evaluated on two different branches, with the first branch comprising an individual pulse analyzer in order to determine information for a PET (Positron Emission Tomography) and the second branch comprising a pulse sequence analyzer in order to determine information for a CT (computer tomography).

SUMMARY OF THE INVENTION

The object underlying the invention is to propose an alternative diagnosis device and an alternative diagnosis method for a combined or combinable radiographic and nuclear medical examination.

This object is achieved by a device and a method with the features of the independent claims. Advantageous or preferred embodiments are described by the subclaims.

The diagnosis device according to the invention is designed for a combined and/or combinable radiographic and nuclear medical examination. The radiographic examination is preferably designed as an x-ray projection examination. Both the radiographic and also the nuclear medical examination preferably comprise digital imaging methods.

The diagnosis device comprises an x-ray source, which generates x-rays of the human body for examination purposes. The x-ray source is preferably designed as an x-ray tube, preferably having x-ray voltages from 50 to 150 kV, which, in particular, produce x-ray quanta with energy of approximately 40 to 140 keV.

Furthermore, an examination room is provided, which serves to accommodate a patient. For the nuclear medical examination and prior to the start of the examination, radioactive materials are placed in the patient's body in the tissue/organ to be examined, with the aid of suitable radiopharmacs. These radiopharmacs and/or radioactive materials emit gamma radiation (high energy photons). By way of example, the Isotop 99Tc is used, which emits gamma quanta with energies of approximately 140 keV.

In other words, the energies of the x-ray quanta of the x-ray source and the energies of the gamma quanta lie in a similar energy range, in particular from 50 to 160 keV and are thus of a physically similar nature. For distinction purposes, the expressions x-rays, x-ray quanta etc. within this application nevertheless always relate to photons, which are generated in the x-ray source and the expressions gamma radiation, gamma quanta etc. always relate to photons which are emitted by radioactive materials placed within the body of the patient.

The diagnosis device comprises a detector system, which is designed to simultaneously measure the x-rays and gamma radiation. The x-ray and gamma quanta can be detected using one and the same detector system, in particular using one and the same detector elements. The detector system preferably comprises a flat detection surface. Alternatively, the detector system is formed from a number of detector elements which are placed one on top of the other and are slightly tilted towards one another, so that the complete detector system comprises an slightly curved detection surface, having a radius of curvature greater than the multiple, in particular greater than the threefold distance of the detection system from the central point of the examination room, with the measurement space of the detector system especially only penetrating the examination room without overlapping. In particular, the detection system does not have a detector arrangement, which is suitable for a PET (positron emission tomography) examination.

On the one hand, the diagnosis device is designed to carry out a classical radiographic examination, in other words an x-ray projection medical examination on the patient. On the other hand, the diagnosis device is designed to carry out a nuclear medical single-photon-emission (SPE) examination on the patient, and to do this without changing the patient's position compared with the x-ray projection medical examination. In the case of the single-photon-emission (SPE) examination known per se, the gamma quanta emitted by the radioactive materials arranged in the body of the patient is detected in an integrating measurement.

The idea underlying the invention is here to create a combination of radiography, in other words an examination using an external radiation source with a high position resolution and a high image quality (high signal-to-noise ratio), with the single-photon-emission (SPE) and/or single-photon-emission-computed tomography (SPECT) method, which enables an organ selective image display. As both methods with the same detector are realized in a system, a total spatial compliance of the examinations are given per design and the overlay of the x-ray and SPE or SPECT images (the latter is also known as scintigraphy images) produces additional diagnostic information for the treating physicians.

With a preferred embodiment of the diagnosis device, an evaluation and control device is provided, which is designed to implement the nuclear medical SPE and/or SPECT examination on the basis of a measurement of the gamma radiation which has been integrated over time. In comparison with a PET examination for instance, an evaluation of individual coincident gamma quanta is not carried out to perform the examination, but instead an evaluation of a gamma quanta flow which has been integrated over time. The radiographic examination is likewise implemented by evaluating an x-ray quanta flow integrated over time.

The diagnosis device is advantageously designed so that combined 2D and/or 3D data sets of the patient can be generated from the two examinations using different radiation types. These data sets comprise locally-resolved information, relating in particular to the skeleton of the patient and organ-selective information.

With a preferred embodiment, the diagnosis device is designed to implement a nuclear medical SPECT examination and a radiographic CT examination. This in particular requires the x-ray source and the detector system to be arranged in a moveable fashion in respect of the patient.

The detector system is preferably designed as a flat panel detector with a sensor matrix and/or pixel matrix. In particular, there is provision for a number of sensors/pixels to be assigned to a common readout channel and/or a common analog/digital converter. With one development of the flat panel detector, provision is made in the circuitry for merging or adding (binning) a number of pixels (e.g. 2×2, 3×3, 4×4), in order to reduce quanta and/or image noises. This binning technique is used particularly to detect the gamma radiation, since, depending on the method, the nuclear medical examination has an inferior local resolution to the radiographic examination, and the merging of pixels only results in slight further deterioration of the local resolution, but produces a considerable improvement in the signal-to-noise ratio.

In a preferred embodiment, the flat panel detector comprises a readout matrix, in particular a TFT matrix, upstream of which is arranged a converter, which converts an incident high-energy photon, i.e. an x-ray quant or a gamma quant, into an electrical charge or a low energy light pulse. The converter is designed in particular as a scintillator.

An integrated signal can be advantageously output by the flat panel detector via an adjustable or controllable integration time for each individual signal and/or for each individual pixel, with the individual sensors and/or the individual pixel in particular being integrated as integrating elements.

With a preferred development, the evaluation and control device is configured so as to control and or mutually synchronize the x-ray source, in particular its emission or exposure time and/or the detector system, in particular the integration time. The evaluation and control device is preferably designed to support or realize a combined recording of radiographic and nuclear medical images: Here, (Option a), the radiographic and nuclear medical examinations and/or their measurements are carried out simultaneously and/or in a temporary overlapping fashion. This is enabled since the flat panel detector registers both the x-rays and also the gamma radiation and does not, in particular, make a distinction between these two radiation types. To achieve similarly high signals, provision can be made to adjust the x-ray dose to the gamma quanta flow, particularly in fact as the x-ray quanta flow is selected to be approximately similarly as great as the gamma quanta flow, or as a short "x-ray flash" is generated for the radiographic examination during the long exposure time for the nuclear medical examination. The x-ray dose and gamma quanta flow are advantageously adjusted by considering the conversion efficiency of the converter in respect of the different energies of the quanta as well as of the different positions of the radiation sources. Alternatively, (Option b), the radiographic and nuclear medical examinations are carried out consecutively and the data sets are subsequently merged.

Provision is optionally made for the evaluation and control device to be designed for 3D imaging, with a common 3D data set or separate 3D data sets first being generated or being able to be generated particularly either from individual images combined from radiographic and nuclear medical measurements as individual images, as they are preferably generated by means of the above-described option a, or with data sets resembling CT resulting from the radiographic measurements and data sets resembling SPECT resulting from the nuclear medical measurements and these then being subsequently merged.

With a practical realization of the diagnosis device, the x-ray source and/or detector system are arranged on actuators, in particular robot arms, for free relative positioning and/or in an annular construction (gantry).

The problem underlying the invention is also solved by a method with the features of the claims. The method according to the invention provides for the use of the already described diagnosis device and additionally for the combined examination to be carried out without changing the patient's position with the common detector system.

BRIEF DESCRIPTION OF THE DRAWINGS

Exemplary embodiments of the invention are explained in more detail below with reference to the drawings, in which.

Elements which correspond to one another are provided with the same reference numerals.

DETAILED DESCRIPTION OF THE INVENTION

Figure 1:
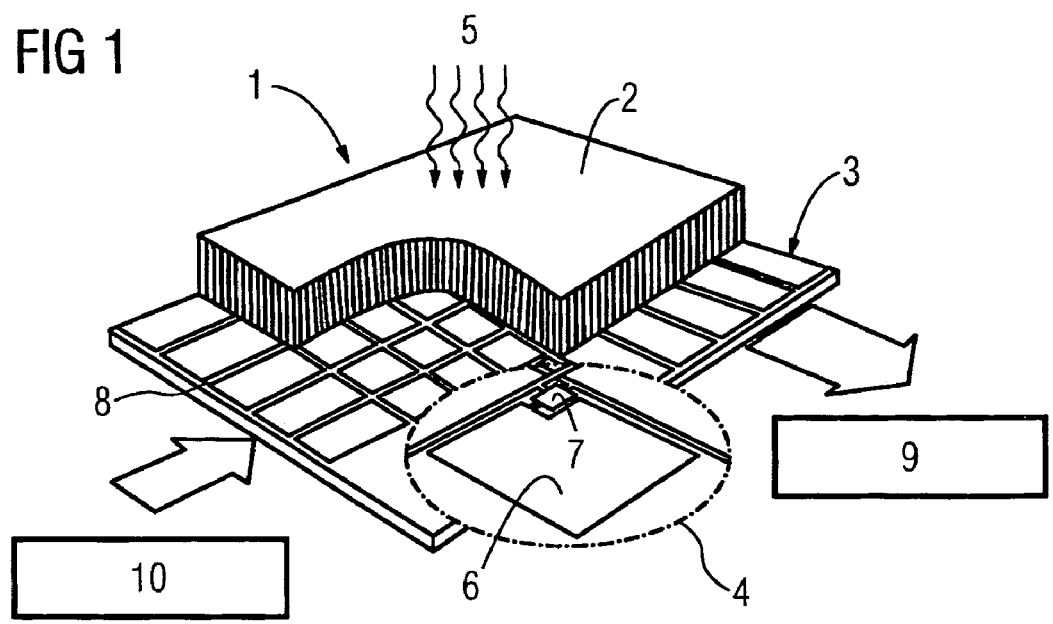
FIG. 1 shows an inclined schematic top view of an exemplary embodiment for a flat panel detector for use in an inventive device.

FIG. 1 shows a schematic 3D top view of an exemplary embodiment of a flat panel detector 1 in the form of a solid body detector, as can be used with an inventive device or an inventive method.

The flat panel detector 1 has a converter 2, which is designed as a cesium iodide (CsI) plate, and a readout matrix arrangement, which comprises a plurality of pixels 4 arranged in rows and columns. The readout matrix arrangement is preferably designed as an active readout matrix, e.g. from amorphous silicon (a-Si).

The pixels 4 of the readout matrix arrangement 3 consist in each instance of a photo diode 6 and a switch 7 connected and/or assigned thereto, which is formed in particular by a TFT (thin film transistor), with the pixels 4, in particular the switches 7, being connected by way of a readout conductor 3 to readout electronics 9, which is only indicated schematically.

Converter 2 and readout matrix arrangement are arranged congruent to one another so that x-rays or gamma radiation 5 in the volume of the converter arriving on the topside of the converter 2 operating as a scintillator are converted into light pulses, which strike the readout matrix arrangement arranged on the underside of the converter 2. The incident light pulses are detected by the photo diodes 6 and converted into electrical signals, which are read out via the readout conductor path 3 to the readout electronics 9. In this way, locally-resolved image information relating to the x-rays or gamma radiation 5 can be measured by the flat panel detector 1.

Alternatively, the converter can be designed such that electrical charges are directly generated when the x-rays or gamma radiation strike it. This is possible for instance in the case of a converter made of selenium, cadmium telluride (CdTe), cadmium zinc telluride (CdZnTe), lead oxide (PbO) or mercury oxide (Hgo). In this embodiment, the readout matrix arrangement is made up of a plurality of electrodes on which the generated charges can be stored and read out in a locally-resolved manner by the evaluation electronics.

Alternatively, CCDs (charge coupled devices), APS ("active pixel sensor") or particularly large surface CMOS-chips are used as readout matrix arrangements.

A control electronics 10 is provided in all embodiments of the flat panel detector 1, by means of which control electronics 10 the integration time of the individual pixel 4 can be adjusted selectively or jointly by way of the control conductor paths 8. An exposure time can thus be predetermined by way of the control electronics 10, during which the intensity of incident x-rays and/or gamma radiation 5 is integrated pixel by pixel over time. Alternatively or in addition, a number of images with a comparatively shorter integration time are recorded immediately one after the other and are cumulated pixel by pixel in the course of the evaluation, in order to improve the signal-to-noise ratio.

Figure 2:
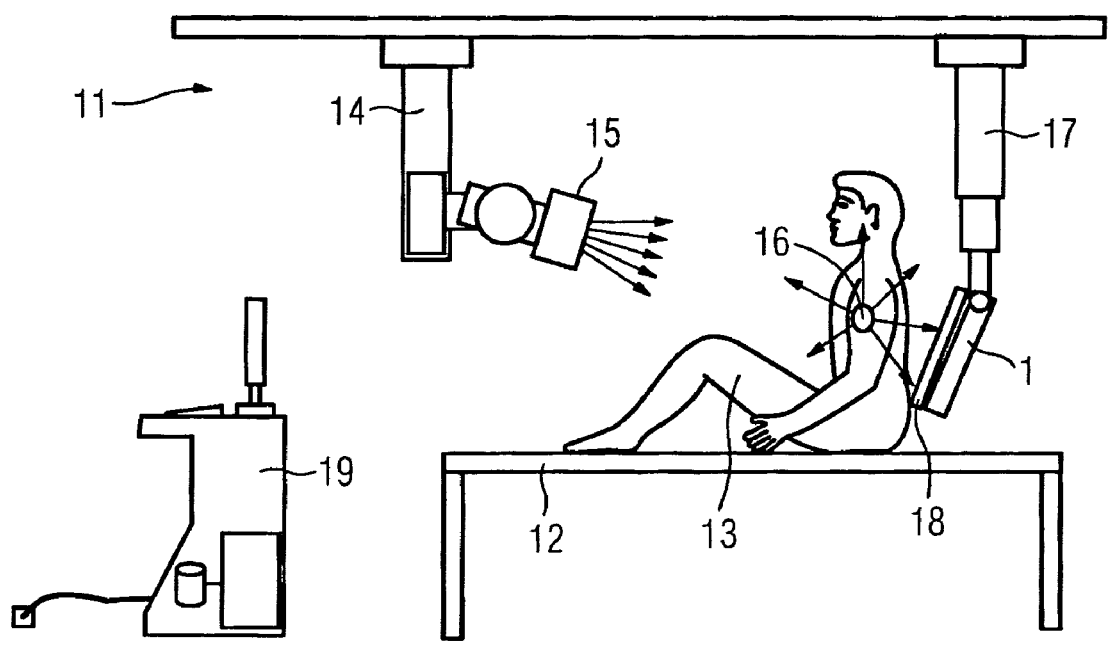
FIG. 2 shows a schematic representation of a first exemplary embodiment for an inventive diagnosis device.

FIG. 2 shows a first exemplary embodiment of an inventive diagnosis device 11 using the flat panel detector 1 in FIG. 1.

The diagnosis device 11 comprises a treatment table 12, on which a patient 13 can be positioned in any position, and is shown in FIG. 2 in a seated position.

An x-ray source 15 arranged on a frame or on the ceiling of the treatment room by way of a robot arm 14 is provided for a radiographic examination of the patient 13. The x-ray source 15 emits x-rays with x-ray quanta of energy of up to approximately 100 keV. Approximately 120 to 150° kV are used as the tube voltage of an x-ray tube in the x-ray source 15 for thorax applications (a higher or lower quanta energy and accordingly a higher or lower x-ray voltage can be required and/or sufficient for other applications). The x-ray source 15 forms an external radiation source in respect of the patient 13.

For a nuclear medical examination, radioactive materials 16 were placed in the tissue and/or organ of the patient to be examined prior to the examination with the aid of adequate radiopharmacs. These radioactive materials 16 emit gamma radiation, in other words high-energy photons. An isotope, for instance the isotope 99Tc, which emits gamma radiation with photons of approximately 140 keV, is used as radioactive material. The radioactive materials 16 form an internal radiation source in respect of the patient 13.

The diagnosis device 11 comprises the flat panel detector 1 in order to detect the x-ray and gamma radiation, said flat panel detector likewise being attached to a frame or the ceiling of the treatment room by way of a second robot arm 17, and operates as a camera with the diagnosis device 11. The illustration in FIG. 2 better shows how the flat panel detector 1 comprises a precisely cuboid basic shape. In particular, the detection surface is designed to be totally flat, i.e. without curves or angles. A scattered radiation grid 18 for filtering out scattered radiation is optionally arranged in front of the flat panel detector 1.

An evaluation and control device 19 is connected to the flat panel detector 1, the x-ray source 15 as well as the robot arms 14 and 17 for the purpose of controlling and transmitting measurement signals. The evaluation and control device 19 in particular comprises a monitor and the system controller. The emission time of the x-ray source 15, the integration time of the flat panel detector 1 and the position and orientation of the robot arms 14 and 17 are controlled using the evaluation and control device 19.

The diagnosis device 11 can be operated in different function modes:

a) SPE-operation: In this function mode, the x-ray source 15 is deactivated and the flat panel detector 1 only registers gamma radiation emanating from the radioactive materials 15. This function mode allows 2-dimensional images of the patient 13 to be produced with an organ-selective representation. The SPE images are in each instance either recorded by a long integration time of the flat panel detector 1 or by the data-specific overlay of several individual recordings recorded one after the other with a minimal integration time by way of adding or averaging.

b) X-ray operation: In this function mode, the x-ray source 15 and simultaneously the flat panel detector 1 are activated temporarily. Typical exposure and integration times are several 100 ms. Additional gamma radiation is registered during the exposure time by way of the flat panel detector 1, the gamma radiation only results in a minimal, negligible disturbance to the x-ray operation as a result of the short exposure time and the minimal radiation flow.

c) combined SPE- and x-ray operation: In this function mode, in an alternative embodiment an SPE and an x-ray image are generated separately and are subsequently overlayed in the evaluation and control device 19 using data processing. With this alternative embodiment, the function modes SPE operation and x-ray operation are run through one after the other. With a further alternative embodiment, the integration time of the flat panel detector 1 is set to the requirements of an SPE individual recording and the x-ray source 15 correspondingly activates the requirements of an x-ray individual recording during the integration time. In other words, with the first alternative, the SPE and x-ray image are combined in the evaluation and control device 19, with the second alternative, the images of the different radiation types are directly integrated in the flat panel detector 1. To compare the different sensitivity of the x-ray and SPE recordings, a comparatively high number of SPE images are advantageously overlayed with only one of a few x-ray images, in the case of the first alternative. In the case of the second alternative, the x-rays only switch in during the long exposure time of the SPE recording for a short amount of time, i.e. for a fraction of the exposure time of the SPE recording.

Provision is optionally made for the flat panel detector to be able to change between different detector modes in respect of the sensitivity for example.

Figure 3:
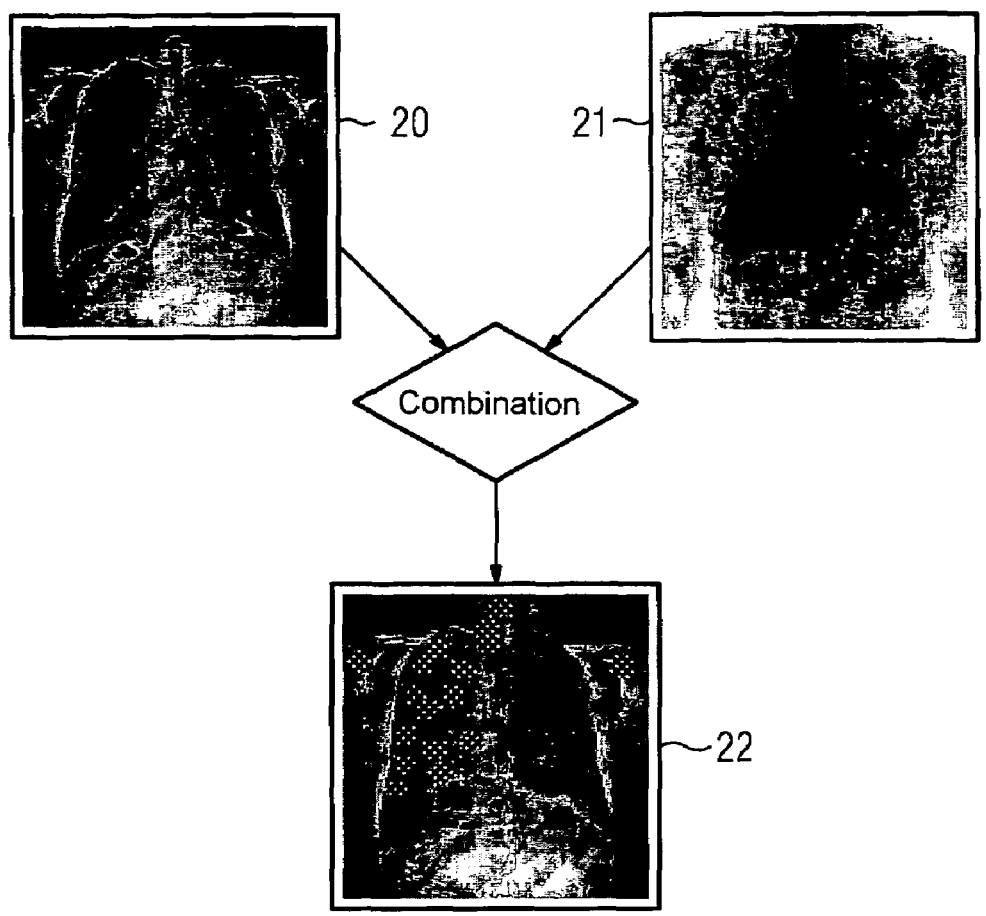
FIG. 3 shows a diagram to illustrate the use of the exemplary embodiment in FIG. 2, FIG. 4 Shows a schematic representation of a second exemplary embodiment for an inventive diagnosis device.

FIG. 3 illustrates a first exemplary embodiment of the method according to the invention using the diagnosis device 11 in FIG. 2. In a first method step, an x-ray image 20 of the patient 13 was produced in the above-described x-ray operation. In a second method step, an SPE image 21 of the patient 13 was produced for the same body region of the patient 13 in the above-described SPE operation. Because the position of the patient 13 remains unchanged during the recording of the two images using the different types of radiation, these images 20 and 21 can be joined to form a combined image 22 with the knowledge of the relative position of the flat panel detector 1 and the x-ray source 15 in the evaluation and control device 19. The combined image 22 thus represents a combination of a classical radiographic image with a classical scintigraphic image. The advantages of the novel device and/or the novel methods lie in the better diagnostic possibilities, since the combined image 22 has a more significance for the treating physician than two separate individual images. Furthermore, the same detector is used for both recording methods (radiography and SPE), thereby resulting in a saving in apparatus.

Figure 4:
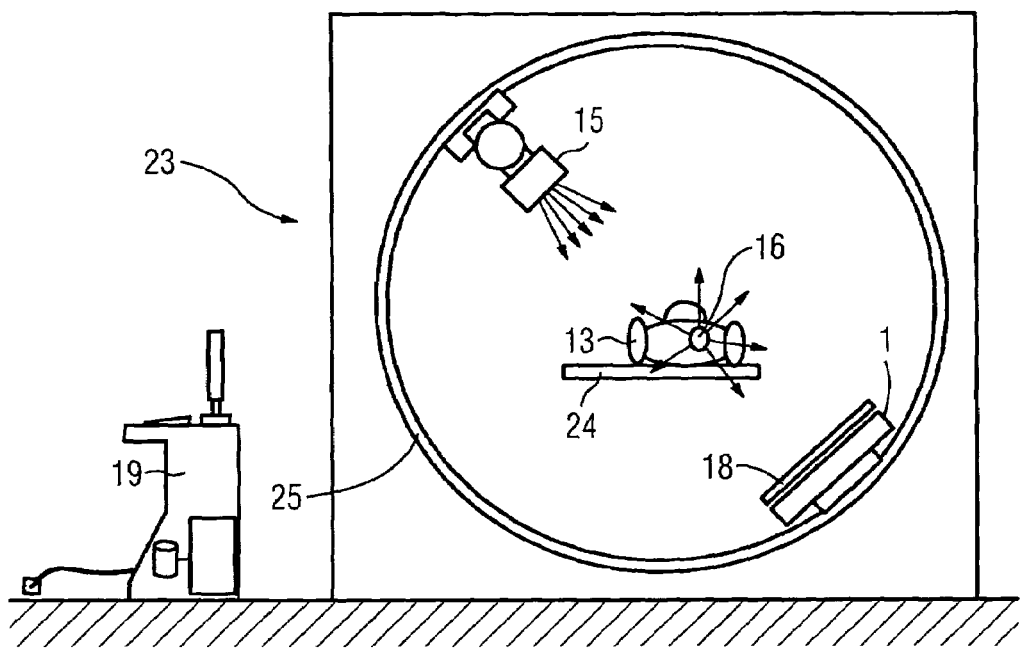

FIG. 4 shows a second embodiment of the device according to the invention in the form of a tomographic diagnosis device 23. In accordance with the diagnosis device 11 in FIG. 3, the tomographic diagnosis device 23 likewise comprises the x-ray source 15, the flat panel detector 1, the evaluation and control device 19 as well as a patient 13 with radioactive material 16 arranged in the body. In contrast to the diagnosis device 11, although the patient 13 lies on a support 24, it is suspended such that the x-ray source 15 arranged opposite to an annular construction (Gantry) 25 or to the end segments of a C-shaped holding device and the flat panel detector 1 can rotate about the patient 13. During rotation, the x-ray source 15 and the flat panel detector 1 are moved in respect of one another in a known manner along the body axis of the patient 13.

The tomographic diagnosis device 23 enables a three-dimensional imaging by using radiographic CT and SPECT methods. As with the diagnosis device 11, different operating modes are also possible using the tomographic diagnosis device 23.

a) SPECT-operation: In this function mode, the x-ray source 15 is deactivated and the flat panel detector 1 only registers gamma radiation emanating from the radioactive materials 16. This function mode allows a 3D data set of the patient 13 to be produced with an organ-selective representation.

b) X-ray operation: In this function mode, the x-ray source 15 and simultaneously the flat panel detector 1 are each activated temporarily and allow a 3D data set of the patient 13 to be produced in a radiographic representation.

c) combined SPECT- and x-ray operation: In this function mode, a SPECT and an x-ray 3D data set are generated separately in an alternative embodiment and are subsequently overlayed in the evaluation and control device 19 in a data-specific manner to form a common 3D data set. With this alternative embodiment, the function modes SPECT operation and x-ray operation are passed through consecutively. The x-ray 3D data set and the SPE 3D data set are advantageously generated using a spatial resolution (binning) which has been adjusted in each instance. With a further alternative embodiment, the radiographic images and the nuclear medical images (scintigraphic images) are first combined, in particular added before a common 3D data set is generated from the combined individual images.

The body position of the patient 13 also remains unchanged during the measurements with the different radiation types with the tomographic diagnosis device 23 and the two radiation types are recorded jointly by the flat panel detector 1, so that the measurement coordinates system is identical and no costly coordinate transformation is required to combine the measurement results from the measurements with the different radiation types.

To enlarge the detector surface of the flat panel detector 1, e.g. for large radiographic recordings, provision can be made to arrange several flat panel detectors, aligned in parallel, next to one another. It is generally advantageous to optimize the pixel size, converter layer thickness etc., such that a good compromise for the two examination methods is found with the different radiation types.

The invention claimed is:

1. A diagnosis device for a medical examination combinable from a radiographic medical examination and a nuclear medical examination on a patient, comprising:
    a gamma radiation source arranged on a body of the patient that emits a gamma radiation;
    an x-ray source that emits an x-ray radiation to the body of the patient;
    a detector system comprising a plurality of detector elements configured to simultaneously measure the x-ray radiation for the radiographic medical examination and the gamma radiation for the nuclear medical examination without changing a position of the patient in an integrating measurement using the identical detector elements, wherein the detector system does not have a detector arrangement for a positron emission tomography examination; and
    an evaluation and control device connected to the x-ray source and the detector system configured to control the radiographic medical examination and the nuclear medical examination being performed consecutively.

2. The diagnosis device as claimed in claim 1, wherein the evaluation and control device comprises a computer program or a circuitry to perform the nuclear medical examination based on the measurement of the gamma radiation which has been integrated with the x-ray radiation over a time period.

3. The diagnosis device as claimed in claim 1, wherein a 2D or 3D image data set of the patient that combines the radiographic medical examination and the nuclear medical examination is generated.

4. The diagnosis device as claimed in claim 1, wherein the nuclear medical examination is a single-photon-emission computer tomography examination or a single-photon-emission examination and the radiographic examination is a computer tomography examination.

5. The diagnosis device as claimed in claim 1, wherein the detector system is a flat panel detector comprising a sensor matrix or a pixel matrix.

6. The diagnosis device as claimed in claim 5, wherein the flat panel detector comprises a readout matrix and a converter.

7. The diagnosis device as claimed in claim 6, wherein the converter is arranged upstream of the readout matrix and converts an incident high-energy photon into an electrical charge or into a low energy light pulse.

8. The diagnosis device as claimed in claim 5, wherein a signal of the nuclear medical examination is integrated with a signal of the radiographic medical examination over an integration time and is output for each individual sensor of the sensor matrix or each individual pixel of the pixel matrix by the flat panel detector.

9. The diagnosis device as claimed in claim 8, wherein the evaluation and control device controls an emission time or exposure time of the x-ray source or the integration time of the detector system for improving a signal to noise ratio of an image recorded by the detector system.

10. The diagnosis device as claimed in claim 1, wherein the evaluation and control device generates a 3D image of the patient from a common 3D data set generated from a combined image of the radiographic medical examination and the nuclear medical examination.

11. The diagnosis device as claimed in claim 1, wherein the evaluation and control device generates a 3D image of the patient from merging a first 3D data set generated from an image of the radiographic medical examination with a second 3D data set generated from an image of the nuclear medical examination.

12. The diagnosis device as claimed in claim 1, wherein the x-ray source is arranged on a first robot arm and the detector system is arranged on a second robot arm.

13. The diagnosis device as claimed in claim 12, wherein the first robot arm and the second robot arm are arranged on a first frame and a second frame respectively or on a ceiling of an examination room and are movable about the patient.

14. The diagnosis device as claimed in claim 1, wherein the x-ray source and the detector system are arranged oppositely on an annular construction that is rotated about the patient.

15. The diagnosis device as claimed in claim 1, wherein the x-ray source and the detector system are arranged oppositely each on one end of a C-shaped holding device that is rotated about the patient.

16. The diagnosis device as claimed in claim 1, wherein the medical examination is a combined examination from the radiographic medical examination and the nuclear medical examination.

17. A diagnosis method for a medical examination combined from a radiographic examination and a single-photon-emission nuclear medical examination, comprising:
   emitting a gamma radiation from a gamma radiation source arranged on a body of the patient;
   emitting an x-ray radiation from a x-ray source to the body of the patient;
   simultaneously measuring the x-ray radiation for the radiographic medical examination by a detector system comprising a plurality of detector elements and the gamma radiation for the nuclear medical examination without changing a position of the patient in an integrating measurement using the identical detector elements, wherein the detector system does not have a detector arrangement for a positron emission tomography examination; and
   consecutively performing the radiographic medical examination and the nuclear medical examination being controlled by an evaluation and control device connected to the x-ray source and the detector system.

18. The diagnosis method as claimed in claim 17, wherein the evaluation and control device generates a 2D or 3D image of the patient from:
   a common 2D or 3D data set generated from a combined image of the patient of the radiographic medical examination and the nuclear medical examination, or
   merging a first 2D or 3D data set generated from an image of the patient of the radiographic medical examination with a second 2D or 3D data set of the patient generated from an image of the nuclear medical examination.

* * * * *